(12) United States Patent
Starkey et al.

(10) Patent No.: US 11,273,079 B2
(45) Date of Patent: Mar. 15, 2022

(54) FOOT SLEEVE

(71) Applicant: NEO G LIMITED, Harrogate (GB)

(72) Inventors: Paul Starkey, Harrogate (GB); Okan Ozturkatalay, Istanbul (TR)

(73) Assignee: NEO G LIMITED, Harrogate (GB)

( * ) Notice: Subject to any disclaimer, the term of this patent is extended or adjusted under 35 U.S.C. 154(b) by 190 days.

(21) Appl. No.: 16/344,944

(22) PCT Filed: Oct. 23, 2017

(86) PCT No.: PCT/GB2017/053189
§ 371 (c)(1),
(2) Date: Apr. 25, 2019

(87) PCT Pub. No.: WO2018/078343
PCT Pub. Date: May 3, 2018

(65) Prior Publication Data
US 2019/0262187 A1    Aug. 29, 2019

(30) Foreign Application Priority Data

Oct. 28, 2016    (GB) ..................... 1618292

(51) Int. Cl.
*A61F 13/00*    (2006.01)
*A61F 13/06*    (2006.01)
(Continued)

(52) U.S. Cl.
CPC .......... *A61F 13/067* (2013.01); *A61F 5/0111* (2013.01); *A61F 13/066* (2013.01); *A61F 13/08* (2013.01)

(58) Field of Classification Search
None
See application file for complete search history.

(56) References Cited

U.S. PATENT DOCUMENTS 5,898,948 A * 5/1999 Kelly ..................... A41B 11/00
                                                    2/239
6,708,348 B1 * 3/2004 Romay ..................... D04B 1/26
                                                    2/239
(Continued)

FOREIGN PATENT DOCUMENTS

AU    2015205859 A1    8/2015
CN    205987974 U      3/2017
(Continued)

OTHER PUBLICATIONS

International Search Report (ISR) for PCT/GB2017/053189 dated Jan. 29, 2018 (6 pages).
(Continued)

*Primary Examiner* — Kim M Lewis
(74) *Attorney, Agent, or Firm* — Shumaker, Loop & Kendrick, LLP

(57) ABSTRACT

A sleeve for use with a foot, the sleeve including a compression portion operable to apply compression to the midfoot region of the foot. The foot sleeve further includes a raised heel support portion for abutment with the base of the heel region of the foot, and a ball portion for abutment with the ball region of the foot. The thickness of the raised heel support portion is greater than the thickness of the ball portion. The foot sleeve can be used for the treatment of plantar fasciitis.

13 Claims, 3 Drawing Sheets

(51) Int. Cl.
*A61F 5/01* (2006.01)
*A61F 13/08* (2006.01)

(56) References Cited

U.S. PATENT DOCUMENTS

| | | | | |
|---|---|---|---|---|
| 7,192,411 | B2* | 3/2007 | Gobet | A61F 13/08 |
| | | | | 2/239 |
| 10,021,919 | B2* | 7/2018 | Spicuzza | A41B 11/007 |
| 2006/0026740 | A1* | 2/2006 | Vargas | A43B 7/146 |
| | | | | 2/239 |
| 2006/0058722 | A1* | 3/2006 | Brown | A61F 5/0111 |
| | | | | 602/61 |
| 2009/0113603 | A1* | 5/2009 | Liu | A41B 11/007 |
| | | | | 2/240 |
| 2009/0165190 | A1 | 7/2009 | Araki et al. | |
| 2012/0283611 | A1* | 11/2012 | Matsuo | A41D 13/06 |
| | | | | 602/27 |
| 2014/0033567 | A1 | 2/2014 | Heathcote et al. | |
| 2014/0058311 | A1* | 2/2014 | Higgins | A61F 13/064 |
| | | | | 602/63 |
| 2016/0242946 | A1 | 8/2016 | Gambardella et al. | |
| 2016/0302491 | A1* | 10/2016 | Campbell | A41B 11/003 |
| 2017/0196737 | A1 | 7/2017 | Riley et al. | |

FOREIGN PATENT DOCUMENTS

| | | | | |
|---|---|---|---|---|
| EP | 0394149 | A1 * | 10/1990 | A41B 11/00 |
| GB | 2438365 | A | 11/2007 | |
| JP | 2000005328 | A | 1/2000 | |
| TW | 201440675 | A | 11/2014 | |
| WO | 2005063062 | A1 | 7/2005 | |
| WO | 2011150166 | A2 | 12/2011 | |
| WO | 2011150166 | A3 | 12/2011 | |
| WO | 2013063554 | A1 | 5/2013 | |
| WO | 20170173441 | A1 | 10/2017 | |

OTHER PUBLICATIONS

Written Opinion for PCT/GB2017/053189 dated Jan. 29, 2018 (5 pages).
GB Search report for GB1618292.5 dated Mar. 21, 2018 (5 pages).
International Preliminary Report on Patentability (IPRP) for PCT/GB2017/053189 dated Apr. 30, 2019 (7 pages).

* cited by examiner

FOOT SLEEVE

FIELD

The present invention relates to a foot sleeve. More specifically, the present invention relates to a foot sleeve for use in the treatment of plantar fasciitis.

BACKGROUND

Plantar fasciitis is a condition caused by damage to the plantar fascia ligaments. The plantar fascia ligaments are thick flat connective tissue that extends from the calcaneus (or heel bone) to the heads of the metatarsal bones at the ball of the foot to support the arch along the plantar (or base) of the midfoot between these regions. Strain to the plantar fascia ligaments can cause it to become weakened, swollen and irritated. Damage to the plantar fascia commonly results in pain around the heel of the foot.

Treatment of plantar fasciitis can require surgical methods such as plantar fasciotomy. However, such invasive methods of treatment are commonly considered to be a last resort.

Non-surgical treatments include medication with non-steroidal anti-inflammatory drugs and injections of corticosteroid. However, such treatments can also be undesirable as they can require injections and carry the risk of adverse side affects, including fascia rupture.

Other non-surgical treatment methods include the use of taping, night splint boots and orthotic foot sleeves. All of these methods allow for non-pharmacological treatment of the condition, although each can have undesirable properties. Taping can be inconvenient as it requires regular time consuming renewal and the application of skill. Night splint boots are bulky and expensive. Orthotic foot sleeves can provide a simpler treatment method, however the form of treatment is limited to the use of compression around the foot.

Therefore, there is a requirement for an improved orthotic foot sleeve for the treatment of planter fasciitis. It is an object of aspects of the present invention to address one or more of the abovementioned or other problems.

SUMMARY

According to a first aspect of the present invention there is provided a sleeve for use with a foot, the sleeve comprising a compression portion operable to apply compression to the midfoot region of the foot;
the foot sleeve further comprising a raised heel support portion for abutment with the base of the heel region of the foot, and a ball portion for abutment with the ball region of the foot, wherein the thickness of the raised heel support portion is greater than the thickness of the ball portion.

According to another aspect of the present invention there is provided the use of the sleeve according to the first aspect of the present invention for the treatment of plantar fasciitis.

Suitably, the sleeve of the present invention is operable to extend in use from above the talus (or ankle bone) to the toes of the foot, preferably up to the metatarsophalangeal joints (MTP) of the forefoot. As such, the sleeve may be considered to comprise an ankle end and a toe end. Between the ankle end and the toe end the sleeve may be operable to abut the rear of the foot, suitably the rear of the heel, the dorsal (or top) of the foot and the plantar (or base) of the foot. For abutment with the base of the foot, the sleeve includes the heel support portion and the ball portion.

The sleeve may comprise an ankle opening operable to allow for arrangement of the sleeve onto the foot. Preferably, the sleeve further comprises a toe opening such that the toes of the foot are able to extend beyond the end of the sleeve in use.

The sleeve may be formed of a textile material, such as knitted fibres. Suitably, the sleeve comprises an integrally knitted textile material operable to extend from above the talus (or ankle bone) to the toes of the foot, preferably up to the metatarsophalangeal joints (MTP) of the forefoot.

The compression portion of the sleeve may be termed a first high compression portion. Suitably the first high compression portion is operable to apply compression to the base of the midfoot. In addition to the first high compression portion of the sleeve, the sleeve may further comprise other compression portions having the same or different levels of compression and operable to apply compression to other areas of the foot.

The sleeve may comprise a second high compression portion arranged to abut the rear of the foot, suitably above the heel. Suitably, the sleeve comprises a low compression portion arranged such as to abut the heel region in use. Preferably, when a second high compression portion is present the heel low compression portion is arranged between the first high compression portion and the second high compression portion, preferably the heel low compression portion does not completely separate the first and second high compression portions. Preferably, the high compression portions meet around the edges of the heel low compression portion.

The sleeve may further comprise a medium compression portion arranged to abut the top of the foot in use. Preferably, the medium compression portion is operable to apply compression to the top of the midfoot.

The sleeve may further comprise a low compression portion operable to abut the top of the foot. Suitably, the sleeve comprises a top low compression portion operable to abut the top of the foot above the subtalar joint. The sleeve may comprise a top low compression portion operable to abut the top of the foot above the heel region, suitably opposite to the heel region and preferably opposite to the low compression portion of the heel region. The sleeve may comprise a top low compression portion operable to abut the top of the forefoot of the foot, suitably above the metatarsal bones. When two or more of the top low compression portions are present, preferably, they are separated by a higher compression portion, such as a medium or high compression portion, preferably by a medium compression portion. More preferably, a medium compression portion separates the top low compression portion(s) from the high compression portion(s).

Preferably, the sleeve comprises low compression portions and/or a smoother textile material around the edges of the openings of the sleeve. Preferably, these portions are annular, extending around the circumferential edge of the sleeve openings. Preferably, the textile material of the edge low compression portions are formed from a smaller denier fibre than adjacent textile material having a higher level of compression. These compression portions may be an exception to the separation between low compression portions on the top of the sleeve and the high compression portions of the base of the sleeve.

The heel low compression portion may comprise lower denier textile material compared to the adjacent textile material of the sleeve having a higher level of compression.

Preferably, the compression portions are symmetrical about the midline of the foot.

The high, medium and low compression portions may apply levels of compression that are relative to each other, i.e. the levels of compression are high>medium>low. Preferably, the levels of compression of each type of portion are in relation to an objective value. For example, a high compression portion may provide 15-30 mmHg of compression, such as >15-25 mmHg, or >15-20 mmHg, a medium compression portion may provide 10-20 mmHg of compression such as 10-<15 mmHg, a low compression portion may provide 0-15 mmHg of compression, such as 0-<10 mmHg.

The compression portion(s) of the sleeve is preferably elastic compression.

Preferably, the compression portion(s) are contained within integrally knitted textile material extending from above the talus (or ankle bone) to the toes of the foot, preferably terminating at the metatarsophalangeal joints (MTP) of the forefoot.

The sleeve of the present invention may be formed from polyamide, polyurethane, polyester, and/or copolymers thereof such as elastane and/or nylon, and/or cotton. Suitably, the compression portion of the sleeve is formed from polyamide, polyurethane, polyester, and/or copolymers thereof such as nylon and/or elastane. Preferably, the higher compression portion comprise higher amount of polyurethane fibre than the lower compression portions.

The heel support portion of the sleeve of the present invention is operable to elevate the heel of the foot relative to the ball of the foot. Using elevation arranged in combination with compression, the sleeve of the present invention can provide improved treatment of plantar fasciitis. The sleeve of the present invention provides a simple, easy to fit, improved orthotic device for the treatment of plantar fasciitis. In addition, the sleeve of the present invention may be used to help alleviate heel pain and arch pain. The sleeve may also be used to help alleviate swelling symptoms.

The heel support portion may have a thickness of between 2 mm and 30 mm, such as between 2 mm and 20 mm or between 2 mm and 15 mm. The thickness of the ball portion of the sleeve may be between 0.2 mm and 5 mm, such as between 0.4 mm and 3 mm, or between 0.5 mm and 2 mm, or between 0.8 mm and 1.5 mm. Preferably, the ratio of the thickness of heel support portion to the thickness of the ball portion is between 20:0.05 and 10:5, such as between 20:1 and 10:3, or between 15:1 and 10:2.

The heel support portion may comprise a heel end arranged to be proximal to the heel region of the foot in use and a toe end arranged to be proximal to the toes, in use, relative to the heel end. The thickness of the heel support portion may vary along the longitudinal length of the support portion from the heel end to the toe end. Suitably, the heel end is thicker than the toe end. The heel end may comprise a thickness of between 2 mm and 30 mm, such as between 3 mm and 20 mm, between 4 mm and 15 mm or between 6 mm and 12 mm. The toe end may comprise a thickness of between 2 mm and 15 mm, such as 2 mm and 10 mm or between 2 mm and 6 mm. Preferably, the ratio of the thickness of the heel end to the toe end is between 10:0.5 and 10:8, such as between 10:1 and 10:5.

It will be appreciated that by the term "end" it is not meant the edge of the heel support portion, but rather a point toward the heel and toe edges.

The heel support portion extends along the sleeve of the present invention such that it abuts the base of the foot in use. Suitably, the heel support portion is arranged to substantially only abut the base of the foot, that is preferably it does not abut the rear of the foot, suitably the rear of the heel.

Suitably, the toe end of the support is spaced by between 2 cm and 15 cm form the edge of the toe end of the support, such as between 3 cm and 10 cm, or between 3.5 cm and 7.5 cm, or between 4 cm and 6 cm. The heel support member may extend along between 20 and 90% of the sleeve operable to abut the base of the foot, such as between 30 and 80%, or between 40 and 70% or between 55 and 65%.

Suitably, the heel support portion comprises an indent in the upper face for abutting the heel, preferably a centrally arranged indent. Preferably, the indent is concave. It will be understood that the indent is preformed in the support, that is it exists in the shape of the support before application to the foot. Advantageously, the indent relieves pressure on the heel.

The heel support portion may comprise a disc, suitably an elongate disc, preferably a moulded polymer disc, suitably it is attached to the textile material of the sleeve. Preferably, the disc is fixedly attached to the textile material, suitably by a cover extending over the disc, wherein the cover is fixedly attached to the textile material of the sleeve such as to hold the disc in position in the sleeve, suitably captively hold the disc in position. The cover of the heel support portion may be fixed to the sleeve using an adhesive or stitching, preferably adhesive. Suitably the cover is formed of a textile material. Preferably, the textile cover substantially completely covers the disc. Preferably, the disc comprises the indent. The disc may be the component of the heel support portion operable to provide the substance of the elevation of the heel in use.

The textile material of the sleeve may have substantially the same thickness along the portion of the sleeve for abutment with the base of the foot, suitably the same thickness between the ankle end and the toe end.

The heal support member may comprise any material operable to maintain a difference in thickness between the heel portion of the sleeve and the ball portion of the sleeve during normal use. Suitably, the heel support portion comprises resiliently deformable material, preferably, the heel support member, and more preferably the polymer disc, is formed from silicone.

Preferably, the ball portion comprises textile material.

The heel support portion, preferably the disc of the heel support portion, may have a horizontal cross section in the form of an oval shape, suitably having a widest point toward the heel end of the support portion.

The width and length of the heel support member depends on the size of the foot for which the sleeve is intended.

All of the features contained herein may be combined with any of the above aspects in any combination.

For a better understanding of the invention, and to show how embodiments of the same may be carried into effect, reference will now be made, by way of example, to the following figures.

DESCRIPTION OF EMBODIMENTS

Figure 1:
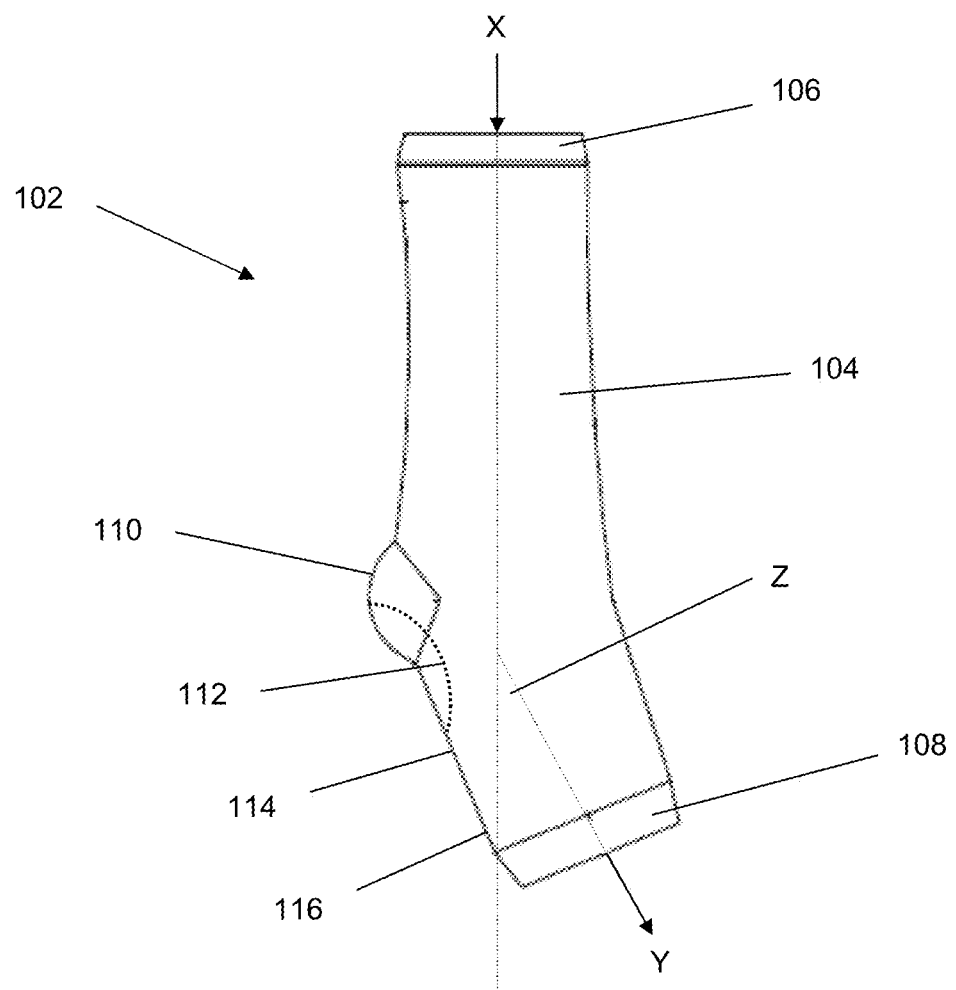
FIG. 1 shows a side view of an embodiment of the sleeve according to the present invention.
Figure 2:
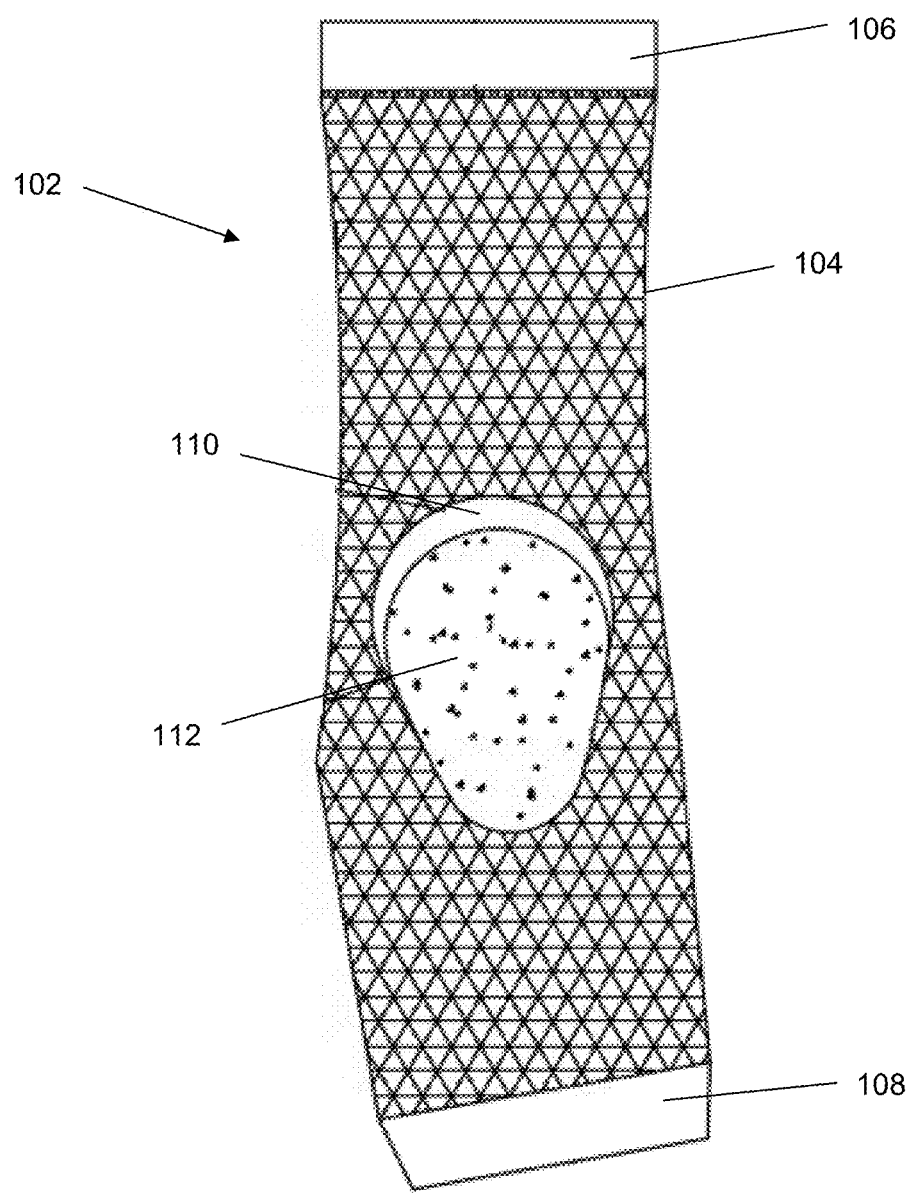
FIG. 2 shows a plan sectional view of the sleeve of FIG. 1.
Figure 3:
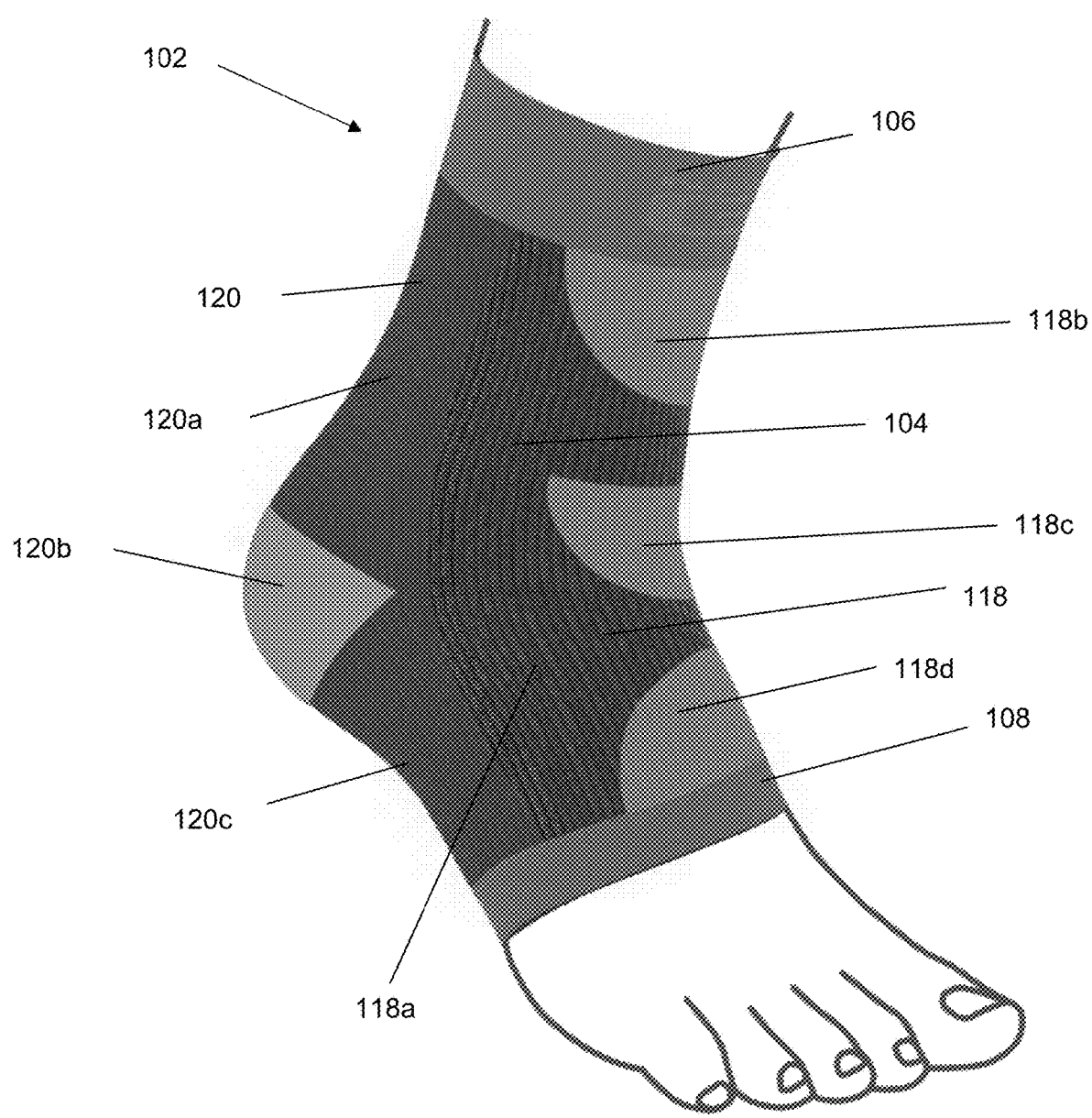
FIG. 3 shoes a perspective side view of the sleeve of FIG. 1 arranged on a foot.

FIGS. 1 to 3 show an embodiment of the foot sleeve 102 of the present invention. Foot sleeve 102 is formed of flexible tubular sleeve 104 having ankle open end 106 and toe open end 108. Sleeve 104 is bent along its longitudinal axis such that open end 108 is offset from diametric opposition to open end 106 by 40° (angle Z). Sleeve 104 is formed of integrally knitted textile material extending continuously from open end 106 to open end 108.

The textile material of sleeve 104 contains several different areas having different levels of compression. The edges of ends 106 and 108 are formed of annular bands of low denier textile material. Arranged on the upper face 118 of sleeve 104 between the bands of ends 106 and 108 are a series of compression portions (not shown) having different levels of compression. A medium compression portion 118a extends along the whole length of the upper face 118 of sleeve 104 between the bands of ends 106 and 108. Extending inwardly from the inner edges of bands 106 and 108 are semi-circular low compression portions 118b and 118d, respectively. The curved edge of low compression portions 118b and d extend away from the inner edge of the bands. Arranged wholly within medium compression portion 118a is a further semi-circular low compression portion 118c which is arranged opposite to the heel portion 110 of the sleeve. The flat edge of low compression portion 118c extends parallel with the edge of ankle end 106 and the curved edge of low compression portion 118c extends toward toe end 108.

Arranged on the bottom face 120 of sleeve 104 are further compression portions having different levels of compression. Around heel portion 110 is arranged low compression portion 120b. Portion 120b is formed of a lower denier textile material than the surrounding compression portions. Between low compression portion 120b and the band of end 106 extends high compression portion 120a and between low compression portion 120b and the band of end 108 extends high compression portion 120c.

Arranged along the bottom face 120 of sleeve 104 between heel portion 110 and the band of end 108 are the portions of the sleeve that abut the base of the midfoot 114 and the ball portion 116, in use.

As shown in FIGS. 1 and 2, arranged on the internal surface of the bottom face 120 of sleeve 104 is oval shaped heel support disc 112. Disc 112 has one end arranged in heel portion 110 at the point at which the sleeve begins to extend upwardly. Disc 112 extends from its heel end 60% of the distance toward the toe end 108 of sleeve 104. After 60% of the distance, the thickness of the sleeve is the same as at the ball portion 116 of sleeve 104.

Disc 112 has a thickness of 10 mm at its heel end and a thickness of 3 mm at the end proximal to toe end 108. Disc 112 generally slopes linearly downwardly from its heel end to its toe end. Disc 112 further contains an indent (not shown), which is the exception to the linear slope. Ball portion 116 has a thickness of 1 mm.

Disc 112 is formed of silicone and is fixedly attached to the textile material of bottom face 120 by a cover (not shown) of textile material that is arranged over disc 112 and fixedly attached to the textile material of face 120 with adhesive.

In use, the user inserts a foot into end 106 (as shown in FIG. 1 as direction X). The foot sleeve 102 is pulled over the foot of the user until disc 112 is arranged under the heel of the foot. As shown in FIG. 3, with sleeve 102 in position over the foot, the toes of the foot will extend from the end 108 (as shown in FIG. 1 as direction Y). Once in position, sleeve 102 elevates the heel of the foot whilst applying compressive pressure. This combination of features allows for an easy improved treatment of plantar fasciitis.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A sleeve for use with a foot having a top face and a base, a heel region, a midfoot region, a forefoot region, a ball region, and a subtalar joint, the sleeve comprising a compression portion operable to apply compression to the midfoot region of the foot, the foot sleeve further comprising a raised heel support portion for abutment with the base of the foot at the heel region, and a ball portion for abutment with the ball region of the foot, wherein the heel support portion and the ball portion each have a thickness and wherein the thickness of the raised heel support portion is greater than the thickness of the ball portion, wherein the sleeve comprises a first high compression portion operable to apply compression to the midfoot region of the foot, and a second high compression portion arranged to abut the rear of the foot.

2. The sleeve according to claim 1, wherein the sleeve is formed of a textile material.

3. The sleeve according to claim 1, wherein the sleeve comprises a heel low compression portion operable to abut the heel region.

4. The sleeve according to claim 3, wherein the heel low compression portion is arranged between the first high compression portion and the second high compression portion.

5. The sleeve according to claim 1, wherein the sleeve further comprises a medium compression portion arranged to abut the top face of the foot.

6. The sleeve according to claim 1, wherein the sleeve further comprises a low compression portion operable to abut the top face of the foot.

7. The sleeve according to claim 1, wherein the sleeve comprises a top face low compression portion operable to abut the top face of the foot above the subtalar joint, a top face low compression portion operable to abut the top face of the foot above the heel region, and/or a top low compression portion operable to abut the top face of the foot above the forefoot.

8. The sleeve according to claim 7, wherein two or more low compression portions are present and the low compression portions are separated by a higher compression portion.

9. The sleeve according to claim 1, wherein a ratio of the thickness of heel support portion to the thickness of the ball portion is between 20:0.05 and 10:5.

10. The sleeve according to claim 1, wherein the heel support portion extends along between 20 and 90% of the sleeve operable to abut the base of the foot.

11. The sleeve according to claim 1, wherein the heel support portion comprises an indent in the upper face for abutting the heel.

12. The sleeve according to claim 1, wherein the heel support portion comprises a disc.

13. The sleeve according to claim 1, wherein the heel support portion has a horizontal cross section in the form of an oval shape.

\* \* \* \* \*